(12) United States Patent
Voll Barclay et al.

(10) Patent No.: US 7,834,228 B1
(45) Date of Patent: Nov. 16, 2010

(54) SYNTHESIS OF MONO-SUBSTITUTED CYCLOPENTADIENES

(75) Inventors: Karin A. Voll Barclay, Boulder, CO (US); Richard D. Crawford, Milliken, CO (US); Dawn A. Arkin, Longmont, CO (US); Daniel A. Gately, Berthoud, CO (US)

(73) Assignee: Boulder Scientific Company, Mead, CO (US)

( * ) Notice: Subject to any disclaimer, the term of this patent is extended or adjusted under 35 U.S.C. 154(b) by 1099 days.

(21) Appl. No.: 11/424,831

(22) Filed: Jun. 16, 2006

Related U.S. Application Data

(60) Provisional application No. 60/691,039, filed on Jun. 16, 2005.

(51) Int. Cl.
*C07C 2/02* (2006.01)
*C07C 1/26* (2006.01)

(52) U.S. Cl. ...................................... 585/375; 585/359

(58) Field of Classification Search ................. 585/359, 585/375
See application file for complete search history.

(56) References Cited

U.S. PATENT DOCUMENTS 5,336,795 A * 8/1994 Lisowsky .................... 556/56
6,175,027 B1 * 1/2001 Sullivan et al. ............... 556/53

OTHER PUBLICATIONS

Stille, John R. and Grubbs, Robert H., Intramolecular Diels-Alder Reaction of alpha,beta-Unsaturated Ester Dienophiles with Cyclopentadiene and the Dependence on Tether Length, J. Org. Chem. 1989, pp. 434-444, vol. 54, No. 2, American Chemical Society, US.

* cited by examiner

*Primary Examiner*—In Suk Bullock
(74) *Attorney, Agent, or Firm*—A Law Firm, P.C.

(57) ABSTRACT

Synthesis of mono-substituted alkylcyclopentadienes by mixing alkyl iodides with cyclopentadienyl magnesium chloride in tetrahydrofuran is described.

19 Claims, No Drawings

SYNTHESIS OF MONO-SUBSTITUTED CYCLOPENTADIENES

CROSS REFERENCE APPLICATIONS

This application is a non-provisional application claiming the benefits of provisional application No. 60/691,039 filed Jun. 16, 2005.

SUMMARY OF THE DISCLOSURE

Alkyl iodides and cyclopentadienylmagnesium chloride in tetrahydrofuran (THF) are mixed, resulting in mono-substituted alkylcyclopentadienes. A desired mono-substituted product can be isolated from the reaction by addition of diluent such as mineral oil to a reaction vessel and simple distillation under vacuum to produce said product in high yield and purity in THF. The disclosed method provides an alternative to isolating the product through water quenching methods of the reaction, phase separating, drying with sodium sulfate and simple distillation. Because the product need not be exposed to water, it is readily useful as a reagent in water sensitive chemistry, i.e., lithiation, Grignard formation, etc. In addition, the disclosed method comprises a one-pot reaction to isolation, which sufficiently improves manufacturing ease and efficiency. In addition to minimizing the risk of dimerization, product storage is improved because the product is formed diluted in THF.

Mono-substituted cyclopentadienes are formed using iodo-compounds. Although chloro- and bromo-compounds may be used, a mixed product profile of mono-, di-, and tri-substituted products could be formed, which may not be easily separated from the desired product in good yield or purity.

There is a need for a cost effective synthesis free of multi-substituted cyclopentadienes, which typically promote a difficult fractional distillation. The disclosed method provides a high yield of mono-substituted cyclopentadienes with high purity.

GENERAL DESCRIPTION OF THE DISCLOSURE

Pursuant to a typical first step of the disclosed method, cyclopentadienyl magnesium chloride (CpMgCl) and iodo-alkyl are added at elevated temperatures to form a mono-substituted cyclopentadiene (Cp). The product is isolated by co-distillation with tetrahydrofuran (THF) from mineral oil. Thus, iodo-alkyls can be mono-substituted in 1:1 stoichiometry with the Cp Grignard. A typical reaction is illustrated by Equation 1:

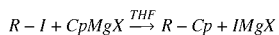

EQUATION 1 wherein, R comprises a $C_1$ to $C_{20}$ alkyl, $C_3$ to $C_{20}$ alkenyl, or $C_7$ to $C_{20}$ alkylaryl. group and X comprises halogen selected from a group consisting of I, Cl, and Br. Although 1:1 stoichiometry is disclosed, a deficiency of the iodo-compound can ensure a clean mono-substituted product. The R groups may be at any available cyclopentadiene ring position. Ring positions not occupied by alkyl, alkenyl, alkylaryl groups may have any other desired substituents. Although Permavis 8™ by Kurt J Lesker Company (a high boiling hydrotreated hydrocarbon oil) may be used, any high boiling hydrocarbon oil, essentially free of volatile components, may be suitable. Synthetic hydrocarbon oils ideally comprising paraffinic or paraffinic/naphthenic components essentially free of olefinic or aromatic components may also be chosen. Although the following examples set forth a variety of reaction temperatures and ranges, the disclosed method may be conducted at temperatures ranging between about 20° C. and the reflux temperature of tetrahydrofuran, which may nominally be about 66° C.

EXEMPLIFICATION OF THE DISCLOSURE

Example 1

Synthesis of n-butylcyclopentadiene

CpMgCl (775.4 g, 0.753 mol) THF solution was added to a reaction flask and warmed to about 30° C. 1-Iodobutane (184 g, 0.72 mol) was fed in and allowed to react at about 30° C. to about 40° C. Reaction was checked for the presence of unsubstituted Cp by quenching a sample on water, phase separating and running on a gas chromatograph (GC), wherein additional iodo-reagent was added until the reaction had achieved completeness. Mineral oil (400 g) was added to the reaction flask. The product was isolated by vacuum distillation and trapping in a chilled receiver. The distillate was analyzed by GC yielding mono-substituted n-butylcyclopentadiene at about 13.3% concentration in THF. The yield of n-butylcyclopentadiene was about 90% by weight. See Equation 2.

EQUATION 2

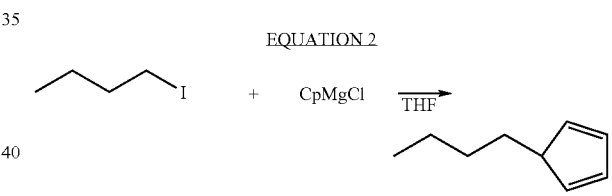

Example 2

Synthesis of ethylcyclopentadiene 975 mLs of CpMgCl/THF (1.05M, 1.02 mol) was added to an addition funnel. A 2 L 3-neck round bottom flask, was charged with ethyl-iodide (155.9 g, 1 mol). The Grignard solution was initially fed in at about 30° C. The pot temperature was held at about 30° C. to about 40° C. by periodic application of ice-water bath. Reaction was checked for the presence of ethyl-iodide by gas chromatograph mass spectrometer (GCMS), wherein additional Grignard was added until the reaction had achieved completeness. The reaction was cooled and quenched with water (300 g). Hexane (100 g, 1.16 mol) was added to the flask to aid in partitioning the organic phase from the aqueous phase. The organic phase was collected in a flask and dried over sodium sulfate and filtered. The product was used as the Hexane/THF solution. The mixture was analyzed by GCMS yielding ethylcyclopentadiene at about 15% concentration in Hexane/THF. The yield of ethylcyclopentadiene was about 60% by weight. See Equation 3.

EQUATION 3

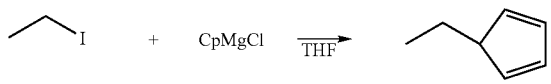

Example 3

Improved Synthesis of ethylcyclopentadiene (Equation 3)

CpMgCl (581.3 g, 0.663 mol) THF solution was concentrated under rough pump in a reaction flask. Iodo-ethane (100 g, 0.64 mol) was added in at elevated temperatures. The pot temperature was tempered at about 30° C. to about 40° C. by periodic application of ice-water bath. Reaction was checked for the presence of iodo-ethane by quenching a sample on water, phase separating and running on a GC, wherein additional Grignard was added until the reaction had achieved completeness. Because the reaction was not complete, three additional shots of Grignard were added. Mineral oil (308 g) was added to the reaction flask. The product was isolated by vacuum distillation. The distillate was analyzed by GC yielding mono-substituted ethylcyclopentadiene at about 14.8% concentration in THF. The yield of ethylcyclopentadiene was about 80.4% by weight.

Example 4

Synthesis of n-but-1-enyl-cyclopentadiene 4-iodo-butene (308.8 g, 1.646 mol) was added to a reaction flask and warmed to a temperature ranging from about 35° C. to about 50° C. 1.707 L CpMgCl (0.995 M, 1.698 mol) was slowly added in at about 35° C. to about 50° C. Reaction was checked for the presence of unreacted 4-iodo-butene by quenching a sample on water, phase separating and running on a GC, wherein additional iodo-reagent was added until the reaction had achieved completeness. The mixture was concentrated by atmospheric distillation of excess THF. Mineral oil (700 ml) was added to the reaction flask. The product was isolated by vacuum distillation in mineral oil. The distillate was analyzed by GC yielding mono-substituted butenyl-cyclopentadiene at about 27% concentration in THF. The yield of n-but-1-enyl-cyclopentadiene was about 91.7% by weight. See Equation 4.

EQUATION 4

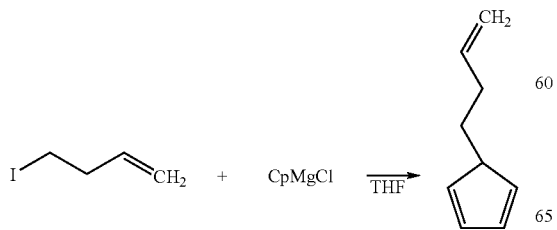

Example 5

Synthesis of n-propylcyclopentadiene

To a 2 L 3-neck round bottomed flask containing 1.079 g CpMgCl (1.03 mol/kg solution, 1.111 mol), 1-Iodopropane (178 g, 1.047 mol) was added dropwise over 45 minutes. The reaction temperature was kept in the range of 30° C. to 40° C. Mineral oil (480 g) was added to the reaction flask. The product was isolated as a THF solution by vacuum distillation from the mineral oil (551 g of co-distillate). The distillate was analyzed by GCMS affording mono-substituted propylcyclopentadiene at 11.4% concentration in THF (62.8 g contained, 58.5% yield). See Equation 5.

EQUATION 5

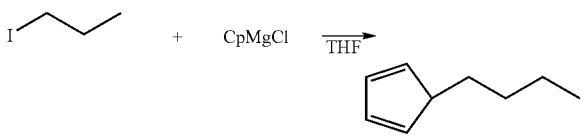

While a number of exemplifying features and embodiments have been discussed above, those with skill in the art will recognize certain modifications, permutations, additions and subcombinations thereof. No limitation with respect to the specific embodiments disclosed herein is intended or should be inferred.

We claim:

1. A process for reacting an organoiodide RI with an ethereal solution of cyclopentadienylmagnesium halide to produce a monosubstituted cyclopentadiene RCp according to the equation RI+CpMgX→RCp+IMgX wherein R comprises a $C_1$ to $C_{20}$ alkyl group, a $C_3$ to $C_{20}$ alkenyl group, or a $C_7$ to $C_{20}$ alkylaryl group, and X comprises a halide; said process further comprising the addition of a hydrocarbon diluent; and wherein said reaction takes place at a temperature ranging from about 20° C. to about 66° C.

2. The process of claim 1 further comprising said reaction occurring at a temperature ranging from about 30° C. to about 50° C.

3. The process of claim 1, wherein the ethereal solution comprises tetrahydrofuran.

4. The process of claim 1, wherein the halide further comprises chloride.

5. The process of claim 1, wherein R is selected from the group consisting of ethyl, n-propyl, n-butyl, and butenyl.

6. A method for producing a monosubstituted cyclopentadiene RCp, said method comprising:

forming a first solution according to the equation

RI+CpMgX→RCp+IMgX wherein R comprises a $C_1$ to $C_{20}$ alkyl group, a $C_3$ to $C_{20}$ alkenyl group, or a $C_7$ to $C_{20}$ alkylaryl group, and X comprises a halide; said reaction taking place at a temperature ranging from about 20° C. to about 66° C.;

treating said first solution with a hydrocarbon diluent to form a second solution; and isolating a mono-substituted cyclopentadiene as distillate from said hydrocarbon-diluted second solution.

7. The method of claim 6, wherein said first solution ranges in temperature between about 30° C. and about 50° C.

8. The method of claim 6, wherein said hydrocarbon diluent further comprises a high boiling hydrocarbon oil, essentially free of volatile components.

9. The method of claim 6, wherein said hydrocarbon diluent further comprises a high boiling hydrotreated hydrocarbon oil, essentially free of olefinic components.

10. The method of claim 6, wherein said first solution further comprises an ethereal solution of CpMgX.

11. The method of claim 10, wherein said first solution further comprises tetrahydrofuran.

12. The method of claim 6, wherein the halide X further comprises chloride.

13. The method of claim 6, wherein R is selected from the group consisting of ethyl, n-propyl, n-butyl, and n-but-1-enyl.

14. The method of claim 6 further comprising a one-pot process.

15. A method for producing a mono-substituted reaction product of the formula

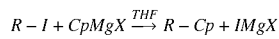

wherein R comprises a $C_1$ to $C_{20}$ alkyl group, a $C_3$ to $C_{20}$ alkenyl group, or a $C_7$ to $C_{20}$ alkylaryl group, and X comprises halogen, said method comprising the step of treating said mono-substituted reaction product with a hydrocarbon diluent and isolating a mono-substituted distillate diluted in said THF.

16. The method of claim 15, wherein said diluent further comprises a high boiling hydrocarbon oil, essentially free of volatile components.

17. The method of claim 15, wherein said reaction takes place at a temperature ranging from about 30° C. to about 50° C.

18. A one-pot process for synthesizing a monosubstituted cyclopentadiene in tetrahydrofuran, said process comprising:
   treating cyclopentadienyl magnesium chloride in tetrahydrofuran with an alkyl iodide to form a reaction mixture comprising mono-substituted alkylcyclopentadiene; and
   treating said reaction mixture with a diluent and isolating said mono-substituted cyclopentadiene in tetrahydrofuran.

19. The process of claim 18, wherein said first treating step takes place at a temperature ranging from about 20° C. to about 66° C.

* * * * *